(12) United States Patent
Miller et al.

(10) Patent No.: US 11,197,871 B2
(45) Date of Patent: *Dec. 14, 2021

(54) METHODS AND MATERIALS FOR TREATING CALCIFIC AORTIC VALVE STENOSIS

(71) Applicant: Mayo Foundation for Medical Education and Research, Rochester, MN (US)

(72) Inventors: Jordan D. Miller, Rochester, MN (US); Bin Zhang, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/717,302

(22) Filed: Dec. 17, 2019

(65) Prior Publication Data

US 2020/0230158 A1  Jul. 23, 2020

Related U.S. Application Data

(60) Continuation of application No. 16/269,628, filed on Feb. 7, 2019, now Pat. No. 10,568,895, which is a continuation of application No. 15/702,461, filed on Sep. 12, 2017, now Pat. No. 10,238,669, which is a division of application No. 14/652,903, filed as application No. PCT/US2013/077254 on Dec. 20, 2013, now Pat. No. 9,789,126.

(60) Provisional application No. 61/740,680, filed on Dec. 21, 2012.

(51) Int. Cl.
| | |
|---|---|
| A61K 31/635 | (2006.01) |
| A61K 31/197 | (2006.01) |
| A61K 31/416 | (2006.01) |
| A61K 31/4985 | (2006.01) |
| A61K 31/506 | (2006.01) |
| A61K 45/06 | (2006.01) |
| A61K 31/519 | (2006.01) |
| A61K 31/5377 | (2006.01) |

(52) U.S. Cl.
CPC .......... *A61K 31/635* (2013.01); *A61K 31/197* (2013.01); *A61K 31/416* (2013.01); *A61K 31/4985* (2013.01); *A61K 31/506* (2013.01); *A61K 31/519* (2013.01); *A61K 31/5377* (2013.01); *A61K 45/06* (2013.01)

(58) Field of Classification Search
USPC ........................................................ 514/158
See application file for complete search history.

(56) References Cited

U.S. PATENT DOCUMENTS

| | | | |
|---|---|---|---|
| 5,250,534 A | 10/1993 | Bell et al. | |
| 5,859,006 A | 1/1999 | Daugan | |
| 6,335,334 B1* | 1/2002 | Schindler | A61P 9/04 514/231.5 |
| 6,670,366 B1 | 12/2003 | Bunnage et al. | |
| 6,699,870 B2 | 3/2004 | Wantanabe et al. | |
| 6,723,719 B1 | 4/2004 | Bunnage et al. | |
| 6,774,128 B2 | 8/2004 | Watkins et al. | |
| 6,825,197 B2 | 11/2004 | Orme et al. | |
| 6,858,620 B2 | 2/2005 | Orme et al. | |
| 6,872,721 B2 | 3/2005 | Orme et al. | |
| 6,878,711 B2 | 4/2005 | Orme et al. | |
| 6,903,099 B2 | 6/2005 | Orme et al. | |
| 6,911,542 B2 | 6/2005 | Orme et al. | |
| 6,916,927 B2 | 7/2005 | Bunnage et al. | |
| 7,014,866 B2 | 3/2006 | Infeld et al. | |
| 9,789,126 B2 | 10/2017 | Miller et al. | |
| 2006/0079502 A1 | 4/2006 | Lang | |
| 2006/0094744 A1 | 5/2006 | Maryanoff et al. | |
| 2011/0028493 A1 | 2/2011 | Matsunaga et al. | |
| 2015/0328235 A1 | 11/2015 | Miller | |
| 2018/0071320 A1 | 3/2018 | Miller et al. | |
| 2019/0183909 A1 | 6/2019 | Miller et al. | |

FOREIGN PATENT DOCUMENTS

| | | |
|---|---|---|
| EP | 2264017 | 12/2010 |
| EP | 2594270 | 5/2013 |
| EP | 2938343 | 9/2018 |
| WO | WO199838168 | 9/1998 |
| WO | WO2003063875 | 8/2003 |
| WO | WO2003101276 | 12/2003 |
| WO | WO2004037183 | 5/2004 |
| WO | WO2005011727 | 2/2005 |
| WO | WO 2013/030564 | 3/2013 |
| WO | WO 2018/064490 | 4/2018 |
| WO | WO 2018/112258 | 6/2018 |

OTHER PUBLICATIONS

Abel et al., "Potential role for P-glycoprotein in the non-proportional pharmacokinetics of UK-343,664 in man," Xenobiotica, 31(8-9):665-676, Aug.-Sep. 2001.

Deguchi et al., "Vasodilator-stimulated phosphoprotein (VASP) phosphorylation provides a biomarker for the action of exisulind and related agents that activate protein kinase G," Mol Cancer Ther., 1(10):803-809, Aug. 2002.

Dukarm et al., "The cGMP-specific phosphodiesterase inhibitor E4021 dilates the pulmonary circulation," Am J Respir Crit Care Med., 160(3):858-865, Sep. 1999.

European Search Report for Application No. 13864299.6, dated Sep. 12, 2016, 5 pages.

(Continued)

*Primary Examiner* — Kathrien A Cruz
(74) *Attorney, Agent, or Firm* — Fish & Richardson P.C.

(57) ABSTRACT

This document provides methods and materials involved in treating cardiovascular conditions such as calcific aortic valve stenosis. For example, methods and materials for using sGC agonists or a combination of sGC agonists and PDE5A inhibitors to reduce calcification of heart valves and/or vessels or to slow progression of aortic sclerosis to calcific aortic valve stenosis are provided.

4 Claims, 7 Drawing Sheets

(56) References Cited

OTHER PUBLICATIONS

Evgenov et al., "NO-independent stimulators and activators of soluble guanylate cyclase: discovery and therapeutic potential," Nat Rev Drug Discov., 5(9):755-768, Sep. 2006.
Freeman et al., "Spectrum of calcific aortic valve disease: pathogenesis, disease progression, and treatment strategies," Circulation, 111(24):3316-3326, Jun. 21, 2005.
Gardiner et al., "Hemodynamic effects of phosphodiesterase 5 and angiotensin-converting enzyme inhibition alone or in combination in conscious SHR," J Pharmacol Exp Ther., 312(1):265-271, Epub Sep. 27, 2004.
International Preliminary Report on Patentability for PCT/US2013/077254, dated Jul. 2, 2015, 6 pages.
International Search Report and Written Opinion for PCT/US2013/077254, dated Apr. 24, 2014, 8 pages.
Lindman et al., "Effects of phosphodiesterase type 5 inhibition on systemic and pulmonary hemodynamics and ventricular function in patients with severe symptomatic aortic stenosis," Circulation., 125(19):2353-2362, Epub Mar. 25, 2012.
Mittendorf et al., "Discovery of riociguat (BAY 63-2521): a potent, oral stimulator of soluble guanylate cyclase for the treatment of pulmonary hypertension," BMC Pharmacology, 9(Suppl 1):P52, Aug. 11, 2009.
Mohler, "Mechanisms of aortic valve calcification," Am J Cardiol., 94(11):1396-1402, A6, Dec. 1, 2004.
Mullershausen et al., "Inhibition of phosphodiesterase type 5 by the activator of nitric oxide-sensitive guanylyl cyclase BAY 41-2272," Circulation, 109(14):1711-1713, Epub Apr. 5, 2004.
Nagayama et al., "Sustained soluble guanylate cyclase stimulation offsets nitric-oxide synthase inhibition to restore acute cardiac modulation by sildenafil," J Pharmacol Exp Ther., 326(2):380-387, Epub May 2, 2008.
Nossaman et al., "Stimulators and activators of soluble guanylate cyclase: review and potential therapeutic indications," Crit Care Res Pract., 2012:290805, Epub Feb. 28, 2012.
Raslan and Mookadam, "The Progression of Aortic Sclerosis to Aortic Stenosis," Aortic Valve, Ch. 6, pp. 121-132, Dec. 9, 2011.
Scutt et al., "EMD273316 & EMD95833, type 4 phosphodiesterase inhibitors, stimulate fibroblastic-colony formation by bone marrow cells via direct inhibition of PDE4 and the induction of endogenous prostaglandin synthesis," BMC Pharmacol., 4:10, Jun. 25, 2004.
Senzaki et al., "Cardiac phosphodiesterase 5 (cGMP-specific) modulates beta-adrenergic signaling in vivo and is down-regulated in heart failure," FASEB J., 15(10):1718-1726, Aug. 2001.
Stasch et al., "Soluble guanylate cyclase as an emerging therapeutic target in cardiopulmonary disease," Circulation., 123(20):2263-2273, May 24, 2011.
Van Eickels et al., "Role of the sGC activator ataciguat sodium (HMR1766) in cardiovascular disease," BMC Pharmacology, 7(Suppl I):S4, 2 pages, 2007.
Walker et al., "Pharmacokinetics and metabolism of a selective PDE5 inhibitor (UK-343,664) in rat and dog," Xenobiotica, 31(8-9):651-664, Aug.-Sep. 2001.
Wang et al., "Phosphodiesterase 5 restricts NOS3/Soluble guanylate cyclase signaling to L-type Ca2+ current in cardiac myocytes," J Mol Cell Cardiol., 47(2):304-314, Epub Apr. 1, 2009.
Zhou et al., "Soluble guanylyl cyclase activation by HMR-1766 (ataciguat) in cells exposed to oxidative stress," Am J Physiol Heart Circ Physiol., 295(4):H1763-71. Epub Aug. 29, 2008.
Mourino-Alvarez et al., "Patients with calcific aortic stenosis exhibit systemic molecular evidence of ischemia, enhanced coagulation, oxidative stress and impaired cholesterol transport," Int. J. Cardiol., Dec. 2016, 225:99-106.
Cowell et al., "A Randomized Trial of Intensive Lipid-Lowering Therapy in Calcific Aortic Stenosis," N. Engl. J. Medicine, Jun. 9, 2005, 352(23):2389-2397.
Rossebø et al., "Intensive Lipid Lowering with Simvastatin and Ezetimibe in Aortic Stenosis," N. Engl. J. Medicine, Sep. 25, 2008, 359(13):1343-1356.

* cited by examiner

METHODS AND MATERIALS FOR TREATING CALCIFIC AORTIC VALVE STENOSIS

CROSS-REFERENCE TO RELATED APPLICATIONS

This application is a continuation of U.S. application Ser. No. 16/269,628, filed Feb. 7, 2019 (now U.S. Pat. No. 10,568,895), which is a continuation of U.S. application Ser. No. 15/702,461, filed Sep. 12, 2017 (now U.S. Pat. No. 10,238,669), which is a divisional of U.S. application Ser. No. 14/652,903, filed Jun. 17, 2015 (now U.S. Pat. No. 9,789,126), which application is a National Stage application under 35 U.S.C. § 371 of International No. PCT/US2013/077254, filed Dec. 20, 2013, which application claims the benefit of U.S. Provisional Application Ser. No. 61/740,680, filed Dec. 21, 2012. The disclosures of the prior applications are considered part of (and are incorporated by reference in) the disclosure of this application.

STATEMENT AS TO FEDERALLY SPONSORED RESEARCH

This invention was made with government support under grant HL092235 awarded by the National Institutes of Health. The government has certain rights in the invention.

BACKGROUND

1. Technical Field

This document relates to methods and materials involved in treating cardiovascular conditions such as calcific aortic valve stenosis. For example, this document provides methods and materials for using soluble guanylate cyclase (sGC) agonists (e.g., oxidized or non-oxidized sGC agonists) or a combination of sGC agonists and cGMP-specific phosphodiesterase 5A (PDE5A) inhibitors to reduce calcification of heart valves and/or vessels or to slow progression of aortic sclerosis to calcific aortic valve stenosis.

2. Background Information

Calcific aortic valve stenosis is a disease where the opening of the aortic valve is narrowed. The symptoms of calcific aortic valve stenosis vary depending on the degree of valve stenosis. Patients with mild to moderate calcific aortic valve stenosis may lack symptoms as symptoms typically appear in those patients with severe calcific aortic valve stenosis. Symptoms can include progressive shortness of breath on exertion, syncope, chest pain, and sudden death.

SUMMARY

This document provides methods and materials involved in treating cardiovascular conditions such as calcific aortic valve stenosis. For example, this document provides methods and materials for using sGC agonists or a combination of sGC agonists and PDE5A inhibitors to reduce calcification of heart valves and/or vessels or to slow progression of aortic sclerosis to calcific aortic valve stenosis. As described herein, sGC agonists such as Ataciguat can be used to slow progression of aortic sclerosis to calcific aortic valve stenosis. Having the ability to slow progression of aortic sclerosis to calcific aortic valve stenosis can allow patients to live longer and happier lives.

In general, one aspect of this document features a method for slowing progression of calcification of a heart valve or vessel. The method comprises, or consists essentially of, (a) identifying a mammal as being at risk for heart valve calcification or vessel calcification, and (b) administering a sGC agonist to the mammal, thereby slowing progression of calcification of a heart valve or vessel within the mammal. The mammal can be a human. The sGC agonist can be selected from the group consisting of YC-I, BAY 58-2667, BAY 41-2272, BAY-41-8543, BAY 63-2521, and HMR1766. The method can comprise administering a PDE5A inhibitor to the mammal.

In another aspect, this document features a method for slowing progression of aortic sclerosis to calcific aortic valve stenosis. The method comprises, or consists essentially of, (a) identifying a mammal having aortic sclerosis, and (b) administering a sGC agonist to the mammal, thereby slowing progression of aortic sclerosis to calcific aortic valve stenosis within the mammal. The mammal can be a human. The sGC agonist can be selected from the group consisting of YC-I, BAY 58-2667, BAY 41-2272, BAY-41-8543, BAY 63-2521, and HMR1766. The method can comprise administering a PDE5A inhibitor to the mammal.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 2A demonstrates the effect of Ataciguat on pVASP239 levels in aortic valve interstitial cells in vitro, and FIG. 2B demonstrates the effect of Ataciguat on BMP2-induced Sp7 expression in aortic valve interstitial cells in vitro. FIG. 2C demonstrates the effects of DDAH1 overexpression on aortic valve function in ldlr-deficient, apoB100-only mice. Overexpression of DDAH1 reduces endogenous inhibitors of NOS, increases NO production, and increases sGC signaling, ultimately resulting in slower progression of CAVS.

DETAILED DESCRIPTION

Figure 1:
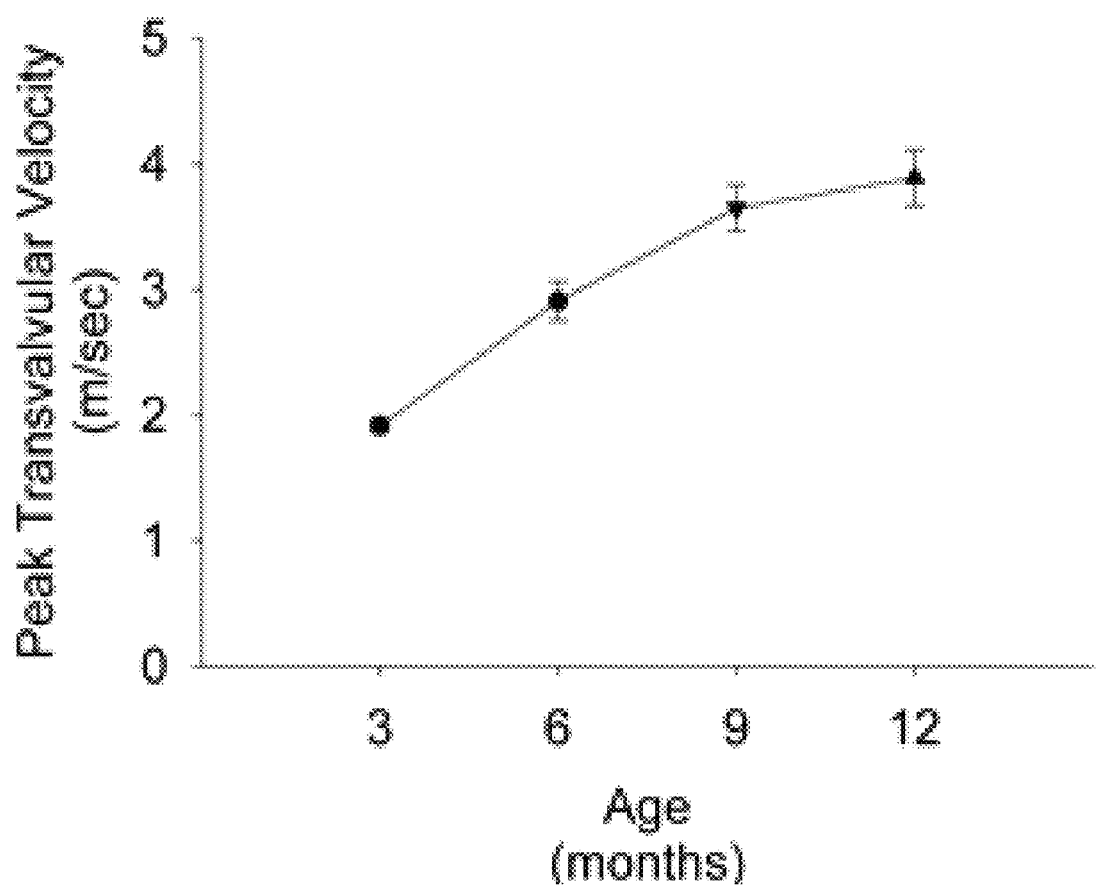
FIG. 1 is a graph plotting the time course of development of calcific aortic valve stenosis in ldlr$^{-/-}$/apoB$^{100/100}$ mice.

This document provides methods and materials involved in treating cardiovascular conditions such as calcific aortic valve stenosis. For example, this document provides methods and materials for using one or more sGC agonists or a combination of one or more sGC agonists and one or more PDE5A inhibitors to reduce calcification of heart valves and/or vessels or to slow progression of aortic sclerosis to calcific aortic valve stenosis.

Any type of mammal having a cardiovascular condition such as calcific aortic valve stenosis can be treated as described herein. For example, humans and other primates such as monkeys having a cardiovascular condition such as calcific aortic valve stenosis can be treated with one or more sGC agonists or a combination of one or more sGC agonists and one or more PDE5A inhibitors. In some cases, dogs, cats, horses, cows, pigs, sheep, mice, and rats can be treated with one or more sGC agonists or a combination of one or more sGC agonists and one or more PDE5A inhibitors as described herein.

Any appropriate method can be used to identify a mammal having a cardiovascular condition such as calcific aortic valve stenosis or aortic sclerosis. For example, echocardiography or computed tomography scanning can be used to identify a human having aortic sclerosis that is at risk of progressing into calcific aortic valve stenosis.

Once identified as having a cardiovascular condition such as calcific aortic valve stenosis or aortic sclerosis with the potential to progress into calcific aortic valve stenosis, the mammal can be administered or instructed to self-administer one or more sGC agonists or a combination of one or more sGC agonists and one or more PDE5A inhibitors. Examples of sGC agonists include, without limitation, Ataciguat, YC-I, BAY 58-2667, BAY 41-2272, and BAY-41-8543. Examples of PDE5A inhibitors include, without limitation, sildenafil, vardenafil, tadalafil, EMD 360527, DA 8159, UK-343-664 (Walker et al., Xenobiotica, 31:651-664 (2001)), UK-427-387, UK-357903 ([1-ethyl-4-{3-[3-ethyl-6,7-dihydro-7-oxo-2-(2-pyridylmethyl)-2H-pyrazolo[4,3-d]pyrimidin-5-yl]-2-(2-methoxyethoxy)-5-pyridylsulphonyl} piperazine]) (Gardiner et al., J. Pharmacol. Exp. Ther., 312:265-271 (2005)), UK-371800 (Pfizer), UK-313794 (Pfizer), UK-343664 (Abel et al., Xenobiotica, 31:665-76 (2001)), TA-1790 (Tanabe Seiyaku), CP-248 (Osi Pharmaceuticals), CP-461 (Osi Pharmaceuticals), exisulind (Deguchi et al., Molecular Cancer Therapeutics, 803-809 (2002); (Osi Pharmaceuticals)), pyrazolinone, EMD82639 (Merck KgaA, Darmstadt, DE; (4-(4-[2-ethyl-phenylamino)-methylene]-3-methyl-5-oxo-4,5-di-hydro-pyrazol-1-yl)-benzoic acid; Senzaki et al., FASEB J., 15:1718-1726 (2001), and Scutt et al., BMC Pharmacol., 4:10 (2004)), EMD360527 (Merck KgaA, Darmstadt, DE; [7-(3-Chloro-4-methoxy-benzylamino)-1-methyl-3-propyl-1H-pyrazolo[4,3-d]pyrimidin-5-ylmethoxy]-acetic acid; Scutt et al., BMC Pharmacol., 4:10 (2004)), EMD221829 (Merck KgaA, Darmstadt, DE; 4-[4-(3-Chloro-4-methoxy-benzylamino)-benzo[4,5]thieno[2,3-d]-pyrimidin-2-yl]-cyclohexanecarboxylic acid, ethanolamin salt; Scutt et al., BMC Pharmacol., 4:10 (2004)), EMD1 71827 (Merck KgaA, Darmstadt, DE; 5-[4-(3-Chloro-4-methoxy-benzylamino)-5,6,7,8-tetrahydro-benzo[4,5]thieno[2,3-d]pyrimidin-2-yl]-pentanoic acid; Scutt et al., BMC Pharmacol., 4:10 (2004)), DA-8259 (3-(1-Methyl-7-oxo-3-propyl-6,7-dihydro-1H-pyrazolo-[4,3-d]pyrimidin-5-yl)-N-[2-(1-methylpyrrolidin-2-yl)ethyl]-4-propoxybenzenesulfonamide), E-4021 (Dukarm et al., Am. J. Respir. Crit. Care Med., 160:858-865 (1999)), pentoxifylline, and FR22934 (Fujisawa). Additional examples of PDE5A inhibitors can be set forth in U.S. Pat. Nos. 6,916,927, 6,911,542, 6,903,099, 6,878,711, 6,872,721, 6,858,620, 6,825,197, 6,774,128, 6,723,719, 6,699,870, 6,670,366, 5,859,006, and 5,250,534 and International Patent Application Publication No. WO 03/063875, WO 03/1012761, WO 2004/037183, and WO 98/38168. In some cases, a sGC agonist used as described herein can be an activator of an oxidized or non-oxidized form of sGC.

In some cases, one or more sGC agonists (e.g., one, two, three, four, five, or more sGC agonists) or a combination of one or more sGC agonists (e.g., one, two, three, four, five, or more sGC agonists) and one or more PDE5A inhibitors (e.g., one, two, three, four, five, or more PDE5A inhibitors) can be administered to a mammal to reduce calcification of heart valves and/or vessels or to slow progression of aortic sclerosis to calcific aortic valve stenosis. In some cases, one or more sGC agonists or a combination of one or more sGC agonists and one or more PDE5A inhibitors can be formulated into a pharmaceutically acceptable composition. For example, a therapeutically effective amount of Ataciguat can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules.

Pharmaceutically acceptable carriers, adjuvants and vehicles that may be used in the pharmaceutical compositions described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. If required, the solubility and bioavailability of a sGC agonist and/or a PDE5A inhibitor in a pharmaceutical composition can be enhanced using lipid excipients and/or block copolymers of ethylene oxide and propylene oxide. See, e.g., U.S. Pat. No. 7,014,866 and U.S. Patent Publication Nos. 20060094744 and 20060079502.

A pharmaceutical composition described herein can be designed for oral or parenteral (including subcutaneous, intramuscular, intravenous, and intradermal) administration. Compositions suitable for parenteral administration include aqueous and non-aqueous sterile injection solutions that can contain anti-oxidants, buffers, bacteriostats, and solutes which render the formulation isotonic with the blood of the intended recipient; and aqueous and non-aqueous sterile suspensions which may include suspending agents and thickening agents. The formulations can be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules, and tablets.

Such injection solutions can be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation can be a sterile injectable solution or suspension in a non-toxic parenterally-acceptable diluent or solvent, for example, as a solution in 1,3-butanediol. Among the acceptable vehicles and solvents that can be used are mannitol, water, Ringer's solution, and isotonic sodium chloride solution. In addition, sterile, fixed oils are conventionally employed as a solvent or suspending medium. For this purpose, any bland fixed oil can be used including synthetic mono- or di-glycerides. Fatty acids, such as oleic acid and its glyceride derivatives can be used in the preparation of injectables, as can natural pharmaceutically-acceptable oils, such as olive oil or castor oil, including those in their polyoxyethylated versions. These oil solutions or suspensions can contain a long-chain alcohol diluent or dispersant.

In some cases, a pharmaceutically acceptable composition including one or more sGC agonists and/or one or more PDE5A inhibitors can be administered locally or systemically. For example, a composition containing a sGC agonist can be administered systemically by injection to a mammal (e.g., a human). In some cases, each sGC agonist to be administered when two or more sGC agonists are to be administered can be administered by the same or different routes. For example, Ataciguat can be administered orally, and YC-I can be administered by injection. In some cases, one or more sGC agonists can be administered via one route, and one or more PDE5A inhibitors can be administered via the same or a different route.

A composition containing one or more sGC agonists or a combination of one or more sGC agonists and one or more PDE5A inhibitors can be administered to a mammal in any amount, at any frequency, and for any duration effective to achieve a desired outcome (e.g., to reduce calcification of heart valves and/or vessels or to slow progression of aortic sclerosis to calcific aortic valve stenosis).

Effective doses can vary, as recognized by those skilled in the art, depending on the severity of the condition (e.g., calcific aortic valve stenosis), the route of administration, the sex, age and general health condition of the subject, excipient usage, the possibility of co-usage with other therapeutic treatments such as use of other agents and the judgment of the treating physician.

An effective amount of a composition containing one or more sGC agonists or a combination of one or more sGC agonists and one or more PDE5A inhibitors can be any amount that reduces the severity of a symptom of a condition being treated (e.g., calcific aortic valve stenosis) without producing significant toxicity to the mammal. For example, an effective amount of a sGC agonist such as YC-I can be from about 0.5 mg/kg to about 80 mg/kg (e.g., from about 0.5 mg/kg to about 70 mg/kg, from about 0.5 mg/kg to about 60 mg/kg, from about 0.5 mg/kg to about 50 mg/kg, from about 0.5 mg/kg to about 40 mg/kg, from about 0.5 mg/kg to about 30 mg/kg, from about 0.5 mg/kg to about 20 mg/kg, from about 0.5 mg/kg to about 10 mg/kg, from about 0.5 mg/kg to about 5 mg/kg, from about 0.5 mg/kg to about 1 mg/kg, from about 0.75 mg/kg to about 10 mg/kg, from about 1 mg/kg to about 10 mg/kg, or from about 2 mg/kg to about 10 mg/kg). In some cases, between about 50 mg and 200 mg (e.g., between about 50 mg and 180 mg, between about 50 mg and 150 mg, between about 50 mg and 125 mg, between about 60 mg and 200 mg, between about 75 mg and 200 mg, between about 100 mg and 200 mg, between about 75 mg and 150 mg, or between about 100 mg and 150 mg) of a sGC agonist such as Ataciguat can be administered to an average sized human (e.g., about 70 kg human) daily for about 20 weeks. If a particular mammal fails to respond to a particular amount, then the amount of sGC agonist or PDE5A inhibitor can be increased by, for example, two fold. After receiving this higher amount, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition (e.g., calcific aortic valve stenosis) may require an increase or decrease in the actual effective amount administered.

The frequency of administration can be any frequency that reduces the severity of a symptom of a condition to be treated (e.g., calcific aortic valve stenosis) without producing significant toxicity to the mammal. For example, the frequency of administration can be from about once a week to about three times a day, or from about twice a month to about six times a day, or from about twice a week to about once a day. The frequency of administration can remain constant or can be variable during the duration of treatment. A course of treatment with a composition containing one or more sGC agonists or a combination of one or more sGC agonists and one or more PDE5A inhibitors can include rest periods. For example, a composition containing one or more sGC agonists or a combination of one or more sGC agonists and one or more PDE5A inhibitors can be administered daily over a two week period followed by a two week rest period, and such a regimen can be repeated multiple times. As with the effective amount, various factors can influence the actual frequency of administration used for a particular application. For example, the effective amount, duration of treatment, use of multiple treatment agents, route of administration, and severity of the condition (e.g., calcific aortic valve stenosis) may require an increase or decrease in administration frequency. An effective duration for administering a composition containing one or more sGC agonists or a combination of one or more sGC agonists and one or more PDE5A inhibitors can be any duration that reduces the severity of a symptom of the condition to be treated (e.g., calcific aortic valve stenosis) without producing significant toxicity to the mammal. Thus, the effective duration can vary from several days to several weeks, months, or years. In general, the effective duration for the treatment of calcific aortic valve stenosis can range in duration from several months to several years. In some cases, an effective duration can be for as long as an individual mammal is alive. Multiple factors can influence the actual effective duration used for a particular treatment. For example, an effective duration can vary with the frequency of administration, effective amount, use of multiple treatment agents, route of administration, and severity of the condition being treated.

In certain instances, a course of treatment and the severity of one or more symptoms related to the condition being treated can be monitored. Any appropriate method can be used to determine whether or not the severity of a symptom is reduced. For example, the severity of a symptom of calcific aortic valve stenosis can be assessed using imaging techniques at different time points.

The invention will be further described in the following examples, which do not limit the scope of the invention described in the claims.

EXAMPLES

Example 1—LDLR$^{-/-}$/apoB$^{100/100}$ Mice Emulate Human Calcific Aortic Valve Stenosis LDLR$^{-/-}$/apoB$^{100/100}$ mice are low density lipoprotein receptor-deficient, apolipoprotein B100-only mice. They were found to develop severe, hemodynamically significant calcific aortic valve stenosis consistently. The peak velocity was about 4 m/sec (FIG. 1). These results indicate that these mice develop stenosis in a manner suitable for studying the effects of pharmacological interventions on initiation and progression of calcific aortic valve stenosis.

Figures 2A, 2B, 2C:
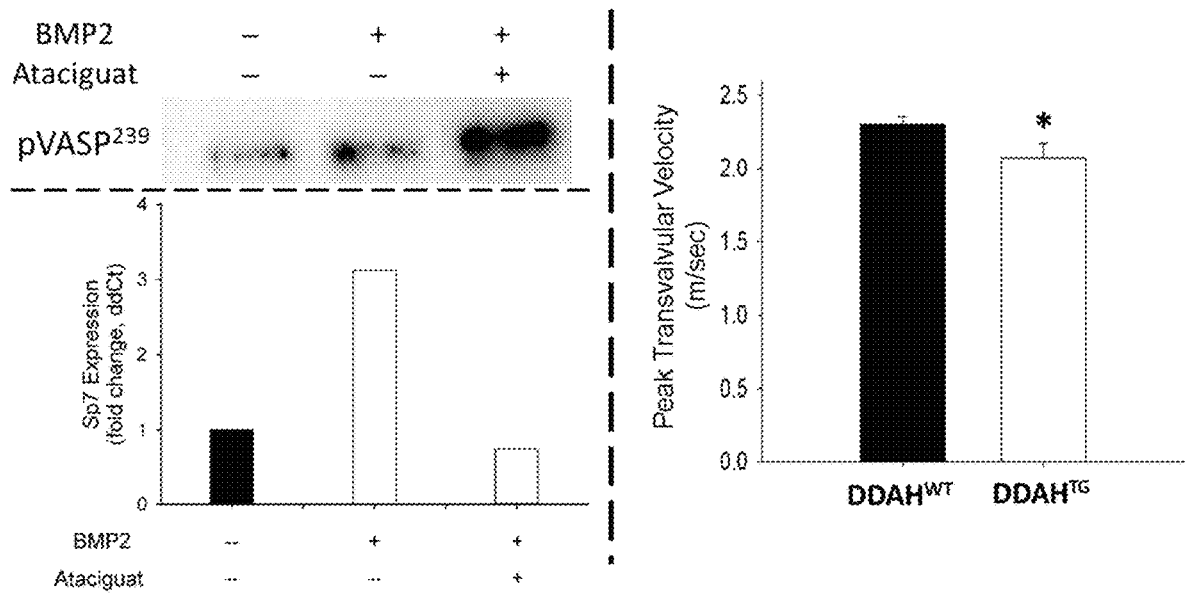
FIGS. 2A-C contain results demonstrating the effects of sGC activation and NO signaling on osteogenic signaling and progression of aortic valve dysfunction in vitro and in vivo.

Example 2—Soluble Guanylate Cyclase Activators Increase NO Signaling which can Slow Progression of Calcific Aortic Valve Stenosis To determine whether induction of sGC signaling reduced osteogenic signaling in vitro, aortic valve interstitial cells were treated with BMP2 in the presence or absence of Ataciguat (HMR1766, 5-Chloro-2-[[(5-chloro-2-thienyl)sulfonyl]amino]-N-[4-(4-morpholinylsulfonyl)phenyl]benzamide) for 24 hours. Ataciguat activated sGC signaling (indicated by pVASP239 levels) and profoundly suppressed osteogenic signaling in aortic valve interstitial cells in vitro (FIGS. 2A and 2B).

To determine whether increasing NO production and sGC signaling can slow progression of calcific aortic valve stenosis in vivo, the effects of overexpressing human DDAH1 (DDAH1TG, an enzyme that degrades endogenous inhibitors of NOS) on aortic valve function in ldlr-deficient, apoB100-only mice were examined. Increasing NO production and sGC signaling in DDAHTG mice slowed progression of calcific aortic valve stenosis (FIG. 2C).

These results demonstrate that soluble guanylate cyclase activators such as Ataciguat activate soluble guanylate cyclase in aortic valve interstitial cells and that increasing NO signaling slows progression of calcific aortic valve stenosis in mammals.

Additional experiments were performed to confirm that Ataciguat activates sGC signaling, attenuates BMP2 signaling, attenuates BMP2 target induction, and attenuates fibrogenic signaling in valve interstitial cells. In brief, cells were maintained in Dulbecco's Modified Eagle's Medium (DMEM) with 20% fetal bovine serum (FBS) and expanded to confluence in 6 well plates in a standard 5% $CO_2$ incubator at 37° C. Cells were then treated with BMP2 (100 ng/mL), TGFβ1 (10 ng/mL), or vehicle (phosphate buffered saline) in the absence or presence of Ataciguat (1 µmol) for 18 hours. Cells were lysed using standard protein lysis buffer containing protease and phosphatase inhibitors, and Western blotting was performed to evaluate changes in protein levels of BMP, TGFβ, and sGC signaling.

Figure 4:
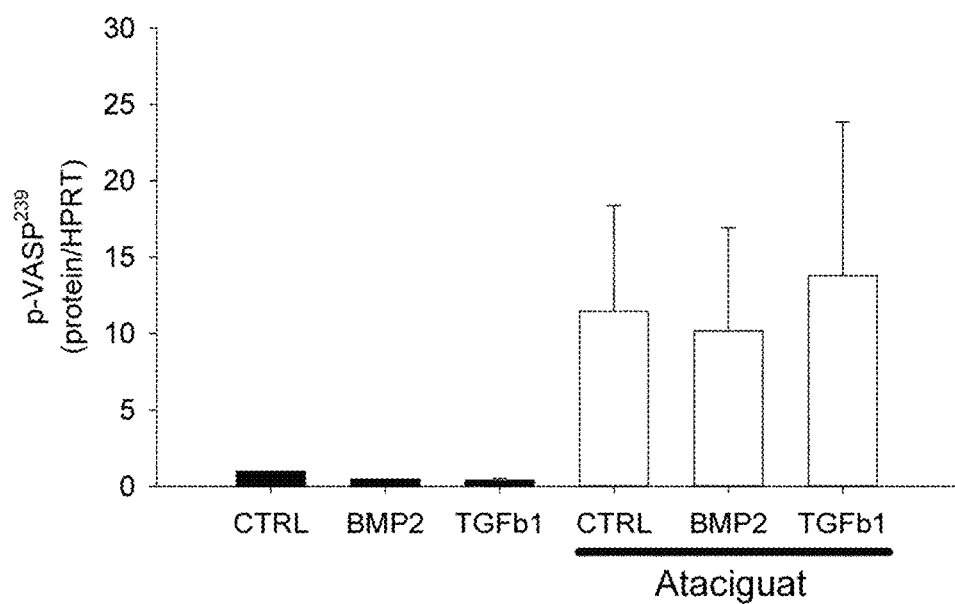
FIG. 4 is a graph plotting p-VASP$^{239}$ levels detected in aortic valve interstitial cells treated with BMP2 (100 ng/mL), TGFβ1 (10 ng/mL), or neither (control; CTRL) in the presence or absence of Ataciguat (1 µmol) for 18 hours at 37° C. Ataciguat (HMR1766) effectively activated sGC signaling in aortic valve interstitial cells.
Figure 5:
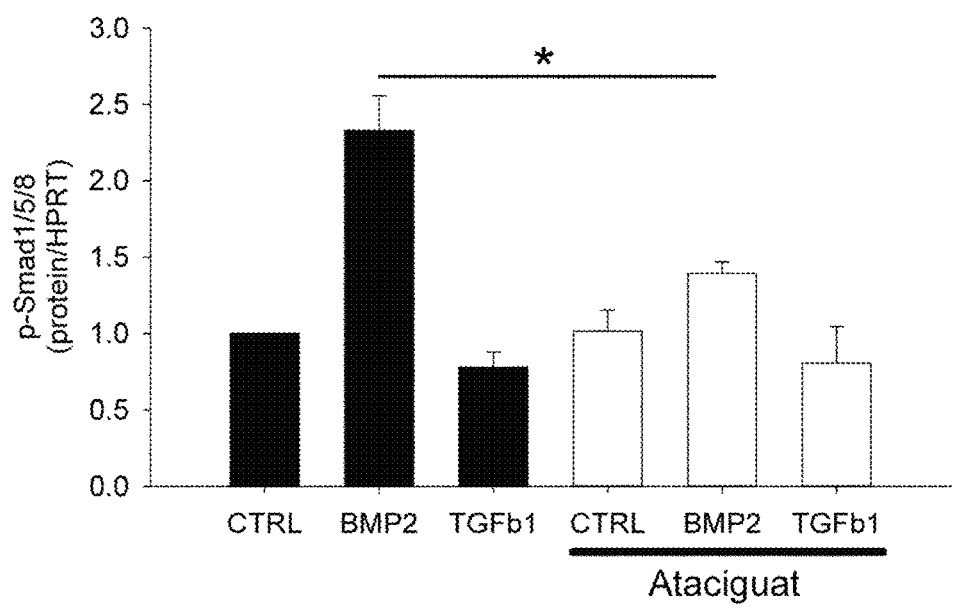
FIG. 5 is a graph plotting p-Smad1/5/8 levels detected in aortic valve interstitial cells treated with BMP2 (100 ng/mL), TGFβ1 (10 ng/mL), or neither (control; CTRL) in the presence or absence of Ataciguat (1 µmol) for 18 hours at 37° C. Ataciguat (HMR1766) attenuated canonical BMP2 signaling in aortic valve interstitial cells.
Figure 6:
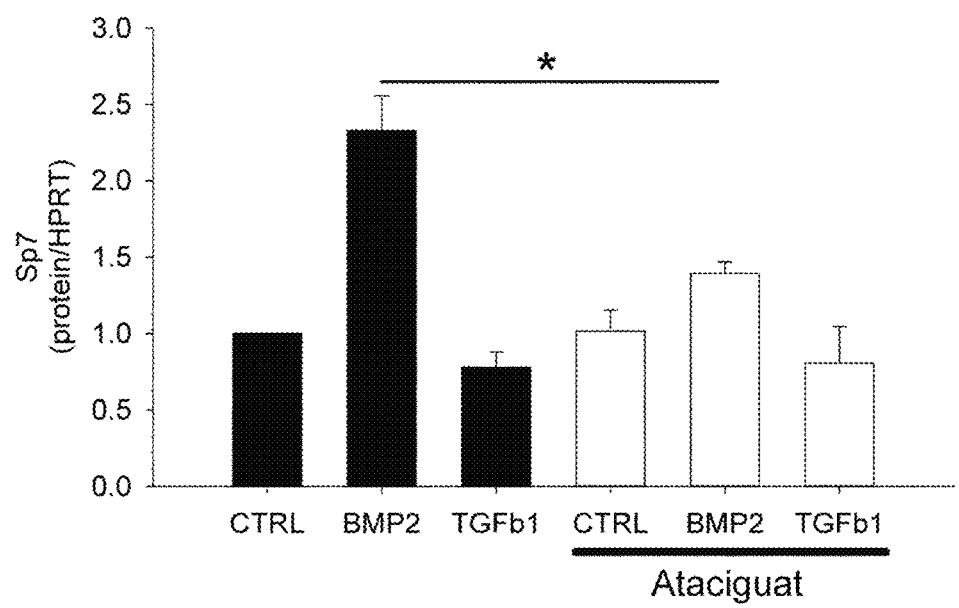
FIG. 6 is a graph plotting Sp7 levels detected in aortic valve interstitial cells treated with BMP2 (100 µg/mL), TGFβ1 (10 µg/mL), or neither (control; CTRL) in the presence or absence of Ataciguat (1 µmol) for 18 hours at 37° C. Ataciguat (HMR1766) attenuated BMP target induction in aortic valve interstitial cells.
Figure 7:
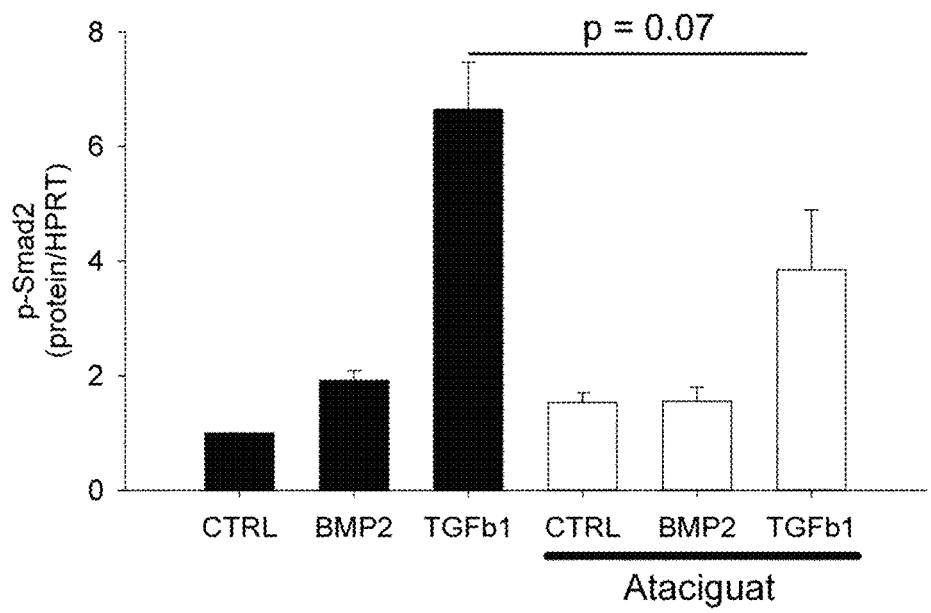
FIG. 7 is a graph plotting p-Smad2 levels detected in aortic valve interstitial cells treated with BMP2 (100 µg/mL), TGFβ1 (10 µg/mL), or neither (control; CTRL) in the presence or absence of Ataciguat (1 µmol) for 18 hours at 37° C. Ataciguat (HMR1766) partially attenuated fibrogenic signaling in aortic valve interstitial cells.

Ataciguat activated sGC signaling (p-VASP[239] levels, FIG. 4), attenuated BMP2 signaling (p-Smad1/5/8, FIG. 5), attenuated BMP2 target induction (Sp7, FIG. 6), and partially attenuated fibrogenic signaling (p-Smad2, FIG. 7) in valve interstitial cells. These results were replicated in human cells lines (HAV-001, HAV-002, HAV-003) and mouse cell lines (MAV1, MAV2, and MAV4).

Figure 3A:
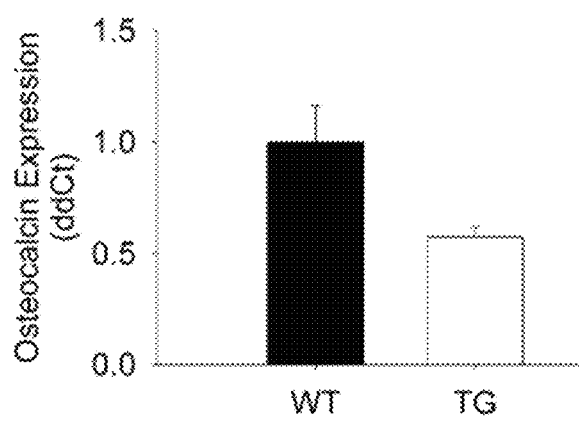
FIGS. 3A-B contain results demonstrating the effects of catalase overexpression or deletion (which would increase or decrease sGC oxidation, respectively) on pro-osteogenic gene expression and aortic valve function in mice. Overexpression of catalase reduces expression of osteocalcin (a pro-osteogenic gene, FIG. 3A) and slows progression of CAVS (open circles, FIG. 3B). Deletion of catalase accelerates valve disease (open squares, FIG. 3B).
Figure 3B:
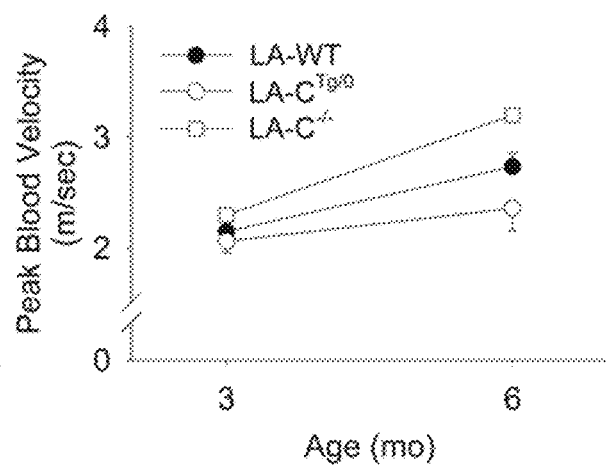

Example 3—Reducing Oxidative Stress Slows Progression of Calcific Aortic Valve Stenosis To determine whether hydrogen peroxide levels are associated with altered osteogenic gene expression and aortic valve dysfunction, ldlr-deficient, apoB100-only mice that either overexpress human catalase or are deficient in catalase were generated. Overexpression of catalase, which reduces oxidative stress, reduced soluble guanylate cyclase oxidation, increased NO signaling, reduced expression of pro-osteogenic genes, and slowed progression of calcific aortic valve stenosis (FIGS. 3A and 3B). Deletion of catalase, which increases oxidative stress, increased sGC oxidation, reduced NO signaling, and accelerated progression of calcific aortic valve stenosis in hypercholesterolemic mice (FIG. 3B).

These results indicate that increases in oxidative stress contribute to soluble guanylate cyclase oxidation, pro-osteogenic gene expression, and progression of calcific aortic valve stenosis in hypercholesterolemic mice.

Example 4—Reducing Pro-Osteogenic Signaling and Slowing Progression of Calcific Aortic Valve Stenosis To confirm that administration of soluble guanylate cyclase activators (e.g., Ataciguat) reduces pro-osteogenic signaling and slows progression of calcific aortic valve stenosis in mammals, ldlr$^{-/-}$/apoB$^{100/100}$ mice are maintained on a Western diet for 6 months, and then are placed into one of four groups: 1) Vehicle, 2) 5 mg/kg Ataciguat/day, or 3) 10 mg/kg Ataciguat/day, or 4) 15 mg/kg Ataciguat/day for an additional 3 months. Vehicle or Ataciguat is administered daily by oral gavage. Changes in cardiac and aortic valve function are evaluated at 3, 6, and 9 months in all four groups of mice. 20 mice of each treatment group are sacrificed at the 9 month time point, which typically represents a stage of moderate to severe calcific aortic valve stenosis in otherwise untreated mice. One group of 10 mice is used for semi-quantitative histological/immunohistochemical evaluation of aortic valve (calcium, osteogenic signaling molecules; n=10). The second group is used for measurement of pro-osteogenic and pro-fibrotic gene expression using qRT-PCR (n=10).

To confirm that soluble guanylate cyclase activators (e.g., Ataciguat) effectively attenuates responses to specific signals that induce osteogenesis in aortic valve interstitial cells, transcriptional responses to various pro-osteogenic molecules in the presence and absence of exogenous oxidative stress (which induce soluble guanylate cyclase oxidation) are examined. In brief, responses to bone morphogenetic protein 2, bone morphogenetic protein 4, and transforming growth factor β-1 (all with or without 100 μM $H_2O_2$) are examined for the ability to be altered by Ataciguat (1 μM). These stimuli are known to be increased in human calcific aortic valve stenosis.

To confirm tolerance of Ataciguat in humans with calcific aortic valve stenosis, patients receiving Ataciguat are monitored. In brief, subjects with asymptomatic, mild-to-moderate calcific aortic valve stenosis are administered placebo, 2.5 mg/kg, 5 mg/kg, or 10 mg/kg Ataciguat (orally) on separate visits and are monitored for 12 hours. Blood pressure is monitored non-invasively and continuously using Dinamap™ and Finapres™ equipment. Every 2 hours, subjects are asked to stand up from sitting or lying down to determine orthostatic tolerance. 40 patients are recruited for this study.

To confirm that Ataciguat can be used to treat calcific aortic valve stenosis, humans with severe calcific aortic valve stenosis are administered placebo or the highest tolerated dose of Ataciguat 24 hours prior to aortic valve replacement surgery. Patients are admitted to the hospital the preceding day to ensure continuous monitoring following this dose. When valve tissue is excised during surgery, a study coordinator takes two small portions of a calcified valve cusp. One is embedded in OCT for cryosectioning, and the second is snap frozen in liquid nitrogen. OCT-embedded tissue is used to determine spatial changes in soluble guanylate cyclase, p-VASP239, and osteogenic protein levels. The second piece is pulverized and is used for quantitative examination of gene expression (qRT-PCR) and protein levels for pro-osteogenic molecules and molecules related to NO-soluble guanylate cyclase signaling.

A randomized, double-blinded study is designed with patients diagnosed with mild to moderate calcific aortic valve stenosis. Patients receive either placebo or Ataciguat. Prior to enrollment in the trial, patients undergo routine, clinically-indicated evaluations of aortic valve and ventricular function using echocardiography and aortic valve calcium using CT imaging. Patients also have blood drawn for evaluation of changes in inflammatory cytokines and circulating p-VASP239 levels. Following 1 month of run-in treatment, patients return for evaluation of tolerance and humoral efficacy (i.e., increases in circulating p-VASP239 levels in treated groups). Aortic valve function and aortic valve calcium burden are evaluated every 6 months by echocardiography and CT imaging, respectively.

Example 5—Using Soluble Guanylate Cyclase Agonists to Slow Progression of Calcification of Heart Valves and Vessels A patient is identified as having aortic valve or vascular calcification through regular echocardiographic screening (typical for a physical exam at age 65 or greater) or following computed tomography scanning of the chest. The patient with evidence of cardiovascular calcification (usually bright, echogenic areas on the valve/vessels) is treated with oral Ataciguat on a daily basis (50 mg/day, 100 mg/day, or 200 mg/day) to slow progression of cardiovascular calcification. P-VASP239 phosphorylation levels in peripheral blood are used to monitor drug bioavailability following 1-2 weeks of treatment. The patient undergos follow-up testing at 1 year with computed tomography scanning to evaluate quantitatively progression of heart valve or vessel calcification. Oral Ataciguat treatment proceeds for the remainder of a subject's lifetime, so long as it is well-tolerated.

Example 6—Using a Combination of Soluble Guanylate Cyclase Agonists and cGMP-Specific Phosphodiesterase 5A Inhibitors to Slow Progression of Calcification of Heart Valves and Vessels A patient is identified as having aortic valve or vascular calcification through regular echocardiographic screening (typical for a physical exam at age 65 or greater) or following computed tomography scanning of the chest. The patient with evidence of cardiovascular calcification (usually bright, echogenic areas on the valve/vessels) is treated with a combination of oral Ataciguat (50 mg/day, 100 mg/day, or 200 mg/day) and a low dose of a PDE5A inhibitor (e.g., Sildenafil or Tadalafil, 2.5 mg/day, 5 mg/day, or 10 mg/day) to slow progression of cardiovascular calcification. P-VASP239 phosphorylation levels in peripheral blood are used to monitor drug bioavailability following 1-2 weeks of treatment. The subject undergoes follow-up testing at 1 year with computed tomography scanning to evaluate quantitatively progression of heart valve or vessel calcification. Treatment with an oral sGCagonist/PDE5A inhibitor combination proceeds for the remainder of a subject's lifetime, as long as it is well-tolerated.

Example 7—Using Soluble Guanylate Cyclase Agonists to Slow Progression of Aortic Sclerosis to Calcific Aortic Valve Stenosis A patient is identified as having aortic valve sclerosis (or mild aortic valve stenosis) through regular echocardiographic screening (typical for a physical exam at age 65 or greater). The patient with evidence of cardiovascular calcification (usually bright, echogenic areas on the valve) is treated with oral sGC activators/stimulators (50 mg/day, 100 mg/day, or 200 mg/day) to slow progression of aortic valve calcification and fibrosis, which can also slow progression of aortic valve dysfunction and progression to aortic valve stenosis. P-VASP239 phosphorylation levels in peripheral blood are used to monitor drug bioavailability following 1-2 weeks of treatment. The subject undergoes follow-up testing at 1 year with echocardiographic imaging to evaluate quantitatively progression of heart valve dysfunction (i.e., reductions in aortic valve area or increases in transvalvular velocity). Treatment with an oral sGC agonist proceeds for the remainder of a subject's lifetime, as long as it is well-tolerated.

Example 8—Using a Combination of Soluble Guanylate Cyclase Agonists and cGMP-Specific Phosphodiesterase 5A Inhibitors to Slow Progression of Aortic Sclerosis to Calcific Aortic Valve Stenosis A patient is identified as having aortic valve sclerosis (or mild aortic valve stenosis) through regular echocardiographic screening (typical for a physical exam at age 65 or greater). The patient with evidence of cardiovascular calcification (usually bright, echogenic areas on the valve/vessels) is treated with a combination of oral Ataciguat (50 mg/day, 100 mg/day, or 200 mg/day) and a low dose of a PDE5A inhibitor (e.g., Sildenafil or Tadalafil, 2.5 mg/day, 5 mg/day, or 10 mg/day) to slow progression of aortic valve calcification and fibrosis, which can also slow progression of aortic valve dysfunction and progression to aortic valve stenosis. P-VASP239 phosphorylation levels in peripheral blood are used to monitor drug bioavailability following 1-2 weeks of treatment. The subject undergoes follow-up testing at 1 year with echocardiographic imaging to evaluate quantitatively progression of heart valve dysfunction (i.e., reductions in aortic valve area or increases in transvalvular velocity). Treatment with an oral sGC agonist/PDE5A inhibitor combination proceeds for the remainder of a subject's lifetime, as long as it is well-tolerated.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for slowing progression of calcification of a heart valve, wherein said method comprises administering a sGC agonist, as the sole active ingredient for slowing said progression, to a mammal identified as having heart valve calcification, thereby slowing progression of calcification of a heart valve within said mammal, wherein the sGC agonist is YC-I (3-(5'-hydroxymethyl-2'furyl)-1-benzyl indazole) or HMR-1766 (5-Chloro-2-[[5-chloro-2-thienyl)sulfonyl]amino]-N-[4-(4-morpholinylsulfonyl)phenyl]benzamide).

2. The method of claim 1, wherein said mammal is a human.

3. The method of claim 1, wherein said sGC agonist is YC-I.

4. The method of claim 1, wherein said sGC agonist is HMR-1766.

* * * * *